(12) United States Patent
Klimko et al.

(10) Patent No.: US 7,923,471 B2
(45) Date of Patent: Apr. 12, 2011

(54) METHOD OF TREATING DRY EYE DISORDERS AND UVEITIS

(75) Inventors: Peter G. Klimko, Fort Worth, TX (US); Mark R. Hellberg, Arlington, TX (US); Daniel A. Gamache, Arlington, TX (US)

(73) Assignee: Alcon, Inc., Hunenberg (CH)

(*) Notice: Subject to any disclaimer, the term of this patent is extended or adjusted under 35 U.S.C. 154(b) by 1555 days.

(21) Appl. No.: 11/268,301

(22) Filed: Nov. 7, 2005

(65) Prior Publication Data

US 2006/0058375 A1 Mar. 16, 2006

Related U.S. Application Data

(63) Continuation-in-part of application No. 11/127,895, filed on May 12, 2005, now abandoned.

(60) Provisional application No. 60/571,162, filed on May 14, 2004.

(51) Int. Cl.
*A01N 37/02* (2006.01)
*A01N 31/00* (2006.01)
*A61K 31/22* (2006.01)
*A61K 31/045* (2006.01)

(52) U.S. Cl. .................................. 514/546; 514/724

(58) Field of Classification Search .................. 514/546, 514/724

See application file for complete search history.

(56) References Cited

U.S. PATENT DOCUMENTS

| | | | |
|---|---|---|---|
| 4,131,651 A | 12/1978 | Shah et al. | 424/78 |
| 4,370,325 A | 1/1983 | Packman | 424/245 |
| 4,409,205 A | 10/1983 | Shively | 424/78 |
| 4,744,980 A | 5/1988 | Holly | 424/78 |
| 4,818,537 A | 4/1989 | Guo | 424/427 |
| 4,883,658 A | 11/1989 | Holly | 424/80 |
| 4,914,088 A | 4/1990 | Glonek et al. | 514/76 |
| 4,966,773 A | 10/1990 | Gressel et al. | 424/489 |
| 5,041,434 A | 8/1991 | Lubkin | 514/182 |
| 5,075,104 A | 12/1991 | Gressel et al. | 424/78.04 |
| 5,174,988 A | 12/1992 | Mautone et al. | 424/45 |
| 5,278,151 A | 1/1994 | Korb et al. | 514/76 |
| 5,290,572 A | 3/1994 | MacKeen | 424/602 |
| 5,294,607 A | 3/1994 | Glonek et al. | 514/76 |
| 5,371,108 A | 12/1994 | Korb et al. | 514/762 |
| 5,441,951 A | 8/1995 | Serhan | 514/213 |
| 5,578,586 A | 11/1996 | Glonek et al. | 514/76 |
| 5,696,166 A | 12/1997 | Yanni et al. | 514/573 |
| 5,800,807 A | 9/1998 | Hu et al. | 424/78.04 |
| 5,958,912 A | 9/1999 | Sullivan | 514/177 |
| 6,153,607 A | 11/2000 | Pflugfelder et al. | 514/178 |
| 6,645,978 B1 | 11/2003 | Gamache et al. | 514/310 |

FOREIGN PATENT DOCUMENTS

| | | |
|---|---|---|
| WO | WO 00/03705 | 1/2000 |
| WO | WO 01/05388 | 1/2001 |
| WO | WO 01/34144 | 5/2001 |

OTHER PUBLICATIONS

Lee et al., "Inhibition of Leukotriene $B_4$-induced Neutrophil Migration by Lipoxin $A_4$: Structure-Function Relationships," *Biiochemical and Biophysical Research Communications*, vol. 180(3), pp. 1416-1421 (1991).

Lemp et al., "Report of the Natioal Eye Institute/Industry Workshop on Clinical Trials in Dry Eyes," *CLAO*, vol. 21(4), pp. 221-231 (1995).

Marsh et al., "Topical Nonpreserved Methylprednisolone Therapy for Keratoconjunctivitis Sicca in Sjogren Syndrome," *Ophthalmology*, vol. 106(1), pp. 811-816 (1999).

McCulley et al., "Tear Film Structure and Dry Eye," *Contactologia*, vol. 20, pp. 145-149 (1998).

Shine et al., "Keratoconjunctivitis Sicca Associated with Meibomian Secretion Polar Lipid Abnormality," *Archives of Ophthalmology*, vol. 116, pp. 849-852 (1998).

Tauber et al., *Lacrimal Gland, Tear Film and Dry Eye Syndromes 2* edited by Sullivan et al., Plenum Press, New York (1998), "A Dose Rangining Clinical Trial to Assess the Safety and Efficacy of Cyclosporine Ophthalmic Emulsion in Patients with Keratoconjunctivitis Sicca," pp. 969-972.

Nan Chiang, et al., "The Lipoxin Receptor ALX: Potent Ligand-Specific and Stereoselective Actions in Vivo," *Pharmacological Reviews*, 2006, pp. 463-487, vol. 58, No. 3.

Fiore, et al., "Induction of Functional Lipoxin A4 Receptors in HL-60 Cells," *Blood*, Jun. 15, 1993, pp. 3395-3403, vol. 81, No. 12.

Karsten Gronert, et al., "Selectivity of Recombinant Human Leukotriene D4, Leukotriene B4, and Lipoxin A4 Receptors with Aspirin-Triggered 15-epi-LXA4 and Regulation of Vascular and Inflammatory Responses," *American Journal of Pathology*, Jan. 2001, pp. 3-9, vol. 158, No. 1.

Karsten Gronert, et al., "A Role for the Mouse 12/15-Lipoxygenase Pathway in Promoting Epithelial Wound Healing and Host Defense," *The Journal of Biological Chemistry*, Apr. 15, 2005, pp. 15267-15278, vol. 280, No. 15.

*Primary Examiner* — Frederick Krass
*Assistant Examiner* — Benjamin Packard
(74) *Attorney, Agent, or Firm* — Patrick M. Ryan

(57) ABSTRACT

The topical use of 5,6,7-trihydroxyheptanoic acid and analogs are disclosed for the treatment of dry eye disorders and uveitis.

9 Claims, No Drawings

METHOD OF TREATING DRY EYE DISORDERS AND UVEITIS

This application is a continuation-in-part of U.S. Ser. No. 11/127,895 filed May 12, 2005 now abandoned, which claims priority to U.S. Provisional Application U.S. Ser. No. 60/571,162 filed May 14, 2004.

The present invention is directed to the treatment of dry eye disorders. In particular, the present invention is directed toward the use of 5,6,7-trihydroxyheptanoic acid and its analogs to treat dry eye and uveitis in mammals.

BACKGROUND OF THE INVENTION

Dry eye, also known generically as keratoconjunctivitis sicca, is a common ophthalmological disorder affecting millions of Americans each year. The condition is particularly widespread among post-menopausal women due to hormonal changes following the cessation of fertility. Dry eye may afflict an individual with varying severity. In mild cases, a patient may experience burning, a feeling of dryness, and persistent irritation such as is often caused by small bodies lodging between the eye lid and the eye surface. In severe cases, vision may be substantially impaired. Other diseases, such as Sjogren's disease and cicatricial pemphigoid manifest dry eye complications.

Although it appears that dry eye may result from a number of unrelated pathogenic causes, all presentations of the complication share a common effect, that is the breakdown of the pre-ocular tear film, which results in dehydration of the exposed outer surface and many of the symptoms outlined above (Lemp, *Report of the National Eye Institute/Industry Workshop on Clinical Trials in Dry Eyes*, The CLAO Journal, volume 21, number 4, pages 221-231 (1995)).

Practitioners have taken several approaches to the treatment of dry eye. One common approach has been to supplement and stabilize the ocular tear film using so-called artificial tears instilled throughout the day. Other approaches include the use of ocular inserts that provide a tear substitute or stimulation of endogenous tear production.

Examples of the tear substitution approach include the use of buffered, isotonic saline solutions, aqueous solutions containing water soluble polymers that render the solutions more viscous and thus less easily shed by the eye. Tear reconstitution is also attempted by providing one or more components of the tear film such as phospholipids and oils. Phospholipid compositions have been shown to be useful in treating dry eye; see, e.g., McCulley and Shine, *Tear film structure and dry eye*, Contactologia, volume 20(4), pages 145-49 (1998); and Shine and McCulley, *Keratoconjunctivitis sicca associated with meibomian secretion polar lipid abnormality*, Archives of Ophthalmology, volume 116(7), pages 849-52 (1998). Examples of phospholipid compositions for the treatment of dry eye are disclosed in U.S. Pat. No. 4,131,651 (Shah et al.), U.S. Pat. No. 4,370,325 (Packman), U.S. Pat. No. 4,409,205 (Shively), U.S. Pat. No. 4,744,980 and U.S. Pat. No. 4,883,658 (Holly), U.S. Pat. No. 4,914,088 (Glonek), U.S. Pat. No. 5,075,104 (Gressel et al.), U.S. Pat. No. 5,278,151 (Korb et al.), U.S. Pat. No. 5,294,607 (Glonek et al.), U.S. Pat. No. 5,371,108 (Korb et al.) and U.S. Pat. No. 5,578,586 (Glonek et al.). U.S. Pat. No. 5,174,988 (Mautone et al.) discloses phospholipid drug delivery systems involving phospholipids, propellants and an active substance.

Another approach involves the provision of lubricating substances in lieu of artificial tears. For example, U.S. Pat. No. 4,818,537 (Guo) discloses the use of a lubricating, liposome-based composition, and U.S. Pat. No. 5,800,807 (Hu et al.) discloses compositions containing glycerin and propylene glycol for treating dry eye.

Although these approaches have met with some success, problems in the treatment of dry eye nevertheless remain. The use of tear substitutes, while temporarily effective, generally requires repeated application over the course of a patient's waking hours. It is not uncommon for a patient to have to apply artificial tear solution ten to twenty times over the course of the day. Such an undertaking is not only cumbersome and time consuming, but is also potentially very expensive. Transient symptoms of dry eye associated with refractive surgery have been reported to last in some cases from six weeks to six months or more following surgery.

Aside from efforts directed primarily to the alleviation of symptoms associated with dry eye, methods and compositions directed to treatment of the dry eye condition have also been pursued. For example, U.S. Pat. No. 5,041,434 (Lubkin) discloses the use of sex steroids, such as conjugated estrogens, to treat dry eye conditions in post-menopausal women; U.S. Pat. No. 5,290,572 (MacKeen) discloses the use of finely divided calcium ion compositions to stimulate pre-ocular tear film production; and U.S. Pat. No. 4,966,773 (Gressel et al.) discloses the use of microfine particles of one or more retinoids for ocular tissue normalization.

Some recent literature reports suggest that patients suffering from dry eye syndrome disproportionately exhibit the hallmarks of excessive inflammation in relevant ocular tissues, such as the lacrimal and meibomian glands. The use of various compounds to treat dry eye patients, such as steroids [e.g. U.S. Pat. No. 5,958,912; Marsh, et al., *Topical nonpreserved methylprednisolone therapy for keratoconjunctivitis sicca in Sjogren syndrome*, Ophthalmology, 106(4): 811-816 (1999); Pflugfelder, et. al. U.S. Pat. No. 6,153,607], cytokine release inhibitors (Yanni, J. M.; et. al. WO 0003705 A1), cyclosporine A [Tauber, J. *Adv. Exp. Med. Biol.* 1998, 438 (Lacrimal Gland, Tear Film, and Dry Eye Syndromes 2), 969], and 15-HETE (Yanni et. al., U.S. Pat. No. 5,696,166), has been disclosed.

Uveitis is an intraocular inflammatory condition that is usually limited to the anterior ocular structures, and can be managed with topical corticosteroids. The inflammatory process can extend behind the lens to affect the pars plana, the vitreous cavity, the choroid, and the retina. These intermediate and posterior manifestations are relatively rare but contribute disproportionately to visual morbidity and present serious therapeutic difficulties. Systemic corticosteroids constitute the first line of treatment for most sight-threatening uveitides. Their long term use is limited by universal and debilitating adverse effects. Second-line agents that allow a reduction in steroid use, such as cyclosporin and azathioprine, offer alternative approaches. Unfortunately their use is frequently limited by a narrow therapeutic window and significant adverse side effects.

Lee et. al. have disclosed that compounds 1 and 2 inhibit $LTB_4$-induced chemotaxis of neutrophils as potently as lipoxin $A_4$ [Lee et. al., *Biochemical and Biophysical Research Communications* 1991, 180(3), 1416-21]. Lipoxin $A_4$ and certain analogs thereof have been reported to be anti-inflammatory agents (see for example Serhan et. al., U.S. Pat. No. 5,441,951). Certain lipoxin analogs have been claimed for treating dry eye (Gamache et. al., U.S. Pat. No. 6,645,978 B1). However to the best of our knowledge no compounds of the present invention have been described for treating dry eye or uveitis.

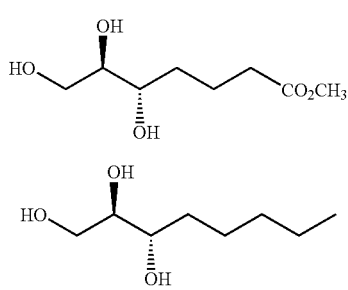

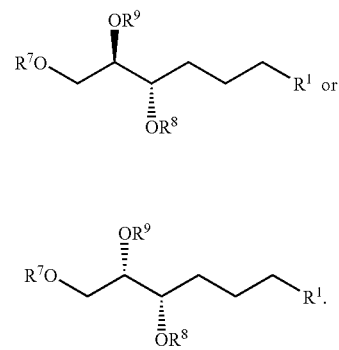

SUMMARY OF THE INVENTION

The present invention is directed to methods for the treatment of dry eye and uveitis. According to the methods of the present invention, a 5,6,7-trihydroxyheptanoic acid or analog is administered to a patient. The 5,6,7-trihydroxyheptanoic acid or analog is preferably administered in an ophthalmic composition dosed topically to a patient's eye.

DETAILED DESCRIPTION OF THE INVENTION

Unless indicated otherwise, all component amounts are presented on a % (w/v) basis.

According to the methods of the present invention, a composition comprising a compound of formula I is topically administered to a mammal in need thereof:

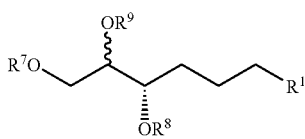

wherein
$R^1$ is $C_2H_5$, $CO_2R$, $CONR^2R^3$, $CH_2OR^4$, or $CH_2NR^5R^6$, where:
  R is H, $C_{1-6}$ straight chain or branched alkyl, $C_{3-6}$ cycloalkyl, or phenyl, or $R^1$ is a carboxylate salt of formula $CO_2^-R^+$, where $R^+$ is $Li^+$, $Na^+$, $K^+$, or an ammonium moiety of formula $^+NR^{10}R^{11}R^{12}R^{13}$;
  $R^2$, $R^3$ are independently H, $C_{1-6}$ alkyl, $C_{3-6}$ cycloalkyl, benzyl, phenyl, OH, $OCH_3$, or $OC_2H_5$, provided that at most only one of $R^2$, $R^3$ is OH, $OCH_3$, or $OC_2H_5$;
  $R^4$ is H, $C(O)R^{14}$, $C_{1-6}$ alkyl, $C_{3-6}$ cycloalkyl, benzyl, or phenyl;
  $R^5$, $R^6$ are independently H, $C(O)R^{14}$, $C_{1-6}$ alkyl, $C_{3-6}$ cycloalkyl, benzyl, phenyl, OH, $OCH_3$, or $OCH_2H_5$, provided that at most only one of $R^5$, $R^6$ is OH, $OCH_3$, or $C_2H_5$;
  $R^7$, $R^8$, and $R^9$ are independently H, $CH_3$, $C_2H_5$, $C(O)R^{14}$, or $CO_2R^{15}$;
  or $R^7$ and $R^8$ or $R^8$ and $R^9$ together constitute a carbonyl group (C=O), thus forming a cyclic carbonate;
  or $OR^8R^1$ together form a cyclic ester (a lactone);
  $R^{10}$-$R^{13}$ are independently H or $C_{1-6}$ alkyl, each alkyl group optionally bearing an OH or $OCH_3$ substituent;
  $R^{14}$ is H, $C_{1-6}$ alkyl, $C_{3-6}$ cycloalkyl, benzyl, or phenyl;
  $R^{15}$ is $C_{1-6}$ alkyl, $C_{3-6}$ cycloalkyl, benzyl, or phenyl; and
  ⸺ indicates that the $OR^9$ substituent can be arranged to afford the R or S absolute configuration:

Preferred compounds of formula I are those wherein:
$R^1$ is $C_2H_5$, $CO_2R$, $CH_2OR^4$, or a carboxylate salt of formula $CO_2^-R^+$;
$R^+$ is $Li^+$, $Na^+$, $K^+$, or $NH_4^+$;
R is H, $CH_3$, $C_2H_5$, n-$C_3H_7$, or i-$C_3H_7$;
$R^4$ is H, $COCH_3$, or $CH_3$; and
$R^7$, $R^8$, $R^9$ are independently H, $CH_3$, $CH_3CO$;
or $R^7$ and $R^8$ or R and $R^9$ together constitute a carbonyl group (C=O), thus forming a cyclic carbonate;
or $OR^8R^1$ together form a cyclic ester (a lactone).

Among the especially preferred compounds are compounds 1-6. Compound 1 is commercially available from Biomol Research Laboratories, Plymouth Meeting, Pa., and compound 2 can be prepared as detailed in Lee et. al., *Biochemical and Biophysical Research Communications* 1991, 180(3), 1416-21. Compounds 3-6 can be prepared as described in examples 14 below.

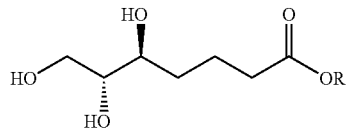

1, R = $CH_3$
4, R = Li
5, R = $C_2H_5$
6, R = i-$C_3H_7$

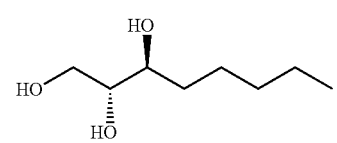

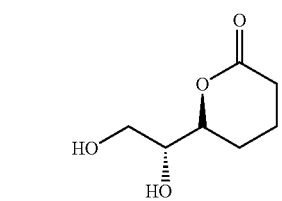

EXAMPLE 1

Synthesis of Compound 3

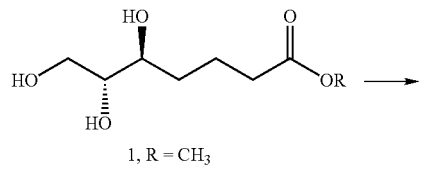

1, R = CH₃

A solution of methyl ester 1 (20 mg, 0.104 mmol) in MeOH (2.1 mL) containing 1 M LiOH (0.5 mL, 0.5 mmol) was heated in a microwave heater at 120° C. for 6 minutes. The reaction was concentrated and the residue was chromatographed on a 10 mm diameter×18 cm tall C18 reverse-phase silica gel column eluting with 7:3 v:v 0.05 M HCl:acetonitrile to afford a crude white solid after concentration (40.9 mg). The solid was rinsed with hot CH₃CN (2×2 mL) and the filtrate was concentrated to afford lactone 3 (7.8 mg, 47%). $^{13}$C NMR (150 MHz, dmso-d₆) δ 171.12 (C), 79.86 (CH), 72.44 (CH), 62.03 (CH₂), 29.39 (CH₂), 21.67 (CH₂), 17.55 (CH₂).

EXAMPLE 2

Synthesis of Compound 4

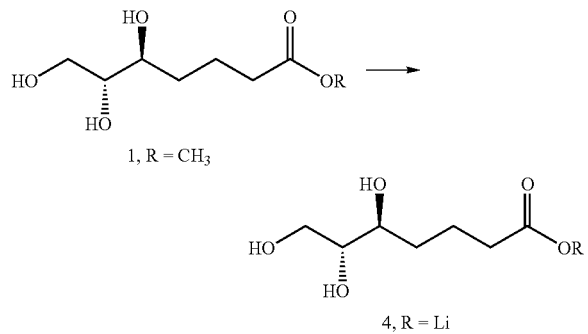

A solution of methyl ester 1 in aqueous MeOH is heated to reflux in the presence of 3 equivalents of lithium hydroxide. After 6 h the reaction is cooled to room temperature and the pH of the solution is adjusted to 6 by the addition of 70-9 mesh sulfonic acid resin MP (commercially available from Novabiochem/EMD Biosciences, 10394 Pacific Center Court, San Diego, Calif. 92121). The solution is filtered through a 0.2 μM poly-terfluoroethylene syringe filter and concentrated to afford the lithium carboxylate 4 as a white solid. $^1$H NMR (D₂O, 400 MHz) δ 3.69-3.64 (m, 1H), 3.55-3.47 (m, 3H), 2.16-2.12 (m, 2H), 1.67-1.64 (m, 1H), 1.54-1.48 (m, 2H), 1.38-1.34 (m, 1H). $^{13}$C NMR (D₂O, 100 MHz) δ 183.46 (C), 74.61 (CH), 71.67 (CH), 62.49 (CH₂), 37.26 (CH₂), 31.55 (CH₂), 22.04 (CH₂).

EXAMPLE 3

Synthesis of Compound 5

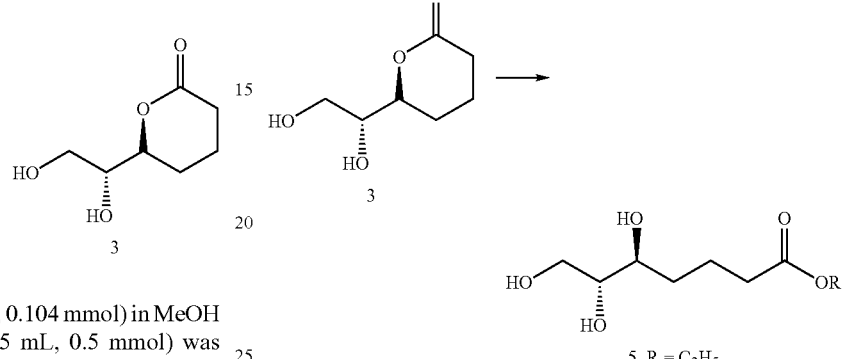

5, R = C₂H₅

A solution of lactone 3 in THF is treated with 3 to 5 equivalents of an ethanolic solution of sodium ethoxide. After 10 h the reaction is quenched by the addition of saturated aqueous potassium dihydrogen phosphate until the pH is about 6. The solution is extracted with ethyl acetate, the organic layer is dried over MgSO₄, filtered, and concentrated, and the residue is chromatographed on a silica gel column to afford ethyl ester 5.

EXAMPLE 4

Synthesis of Compound 6

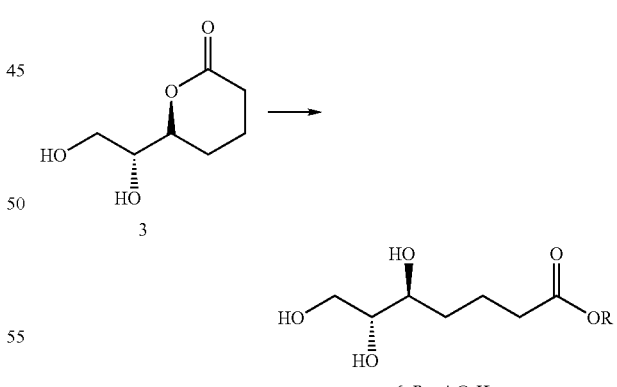

6, R = i-C₃H₇

A solution of lactone 3 in THF is treated with 3 to 5 equivalents of an sodium isopropoxide in isopropanol. After 10 h the reaction is quenched by the addition of saturated aqueous potassium dihydrogen phosphate until the pH is about 6. The solution is extracted with ethyl acetate, the organic layer is dried over MgSO₄, filtered, and concentrated, and the residue is chromatographed on a silica gel column to afford isopropyl ester 6.

EXAMPLE 5

Protective Effect of Compound 1 in a Rabbit Model of Dry Eye

Compound 1 was evaluated in a rabbit model of dry eye. New Zealand white rabbits (approximately 2.5 kg; obtained from Myrtle's Rabbitry, Thompson Station, Tenn.) were randomized and dosed topically twice a day with either 50 µl of compound 1 formulated in 0.064%/BSS® at concentrations of 1, 10, or 100 µM, or with 0.064%/BSS® vehicle. After 24 h the rabbits were anesthetized by subcutaneous administration of ketamine hydrochloride (30 mg/kg) and xylazine (6 mg/kg) and each rabbit received bilateral injections of Conconavilin A (ConA) (300 µg/30 µl) or saline (30 µl). Desiccation was initiated one day following lacrimal gland injection by placing conscious animals in an environmental chamber (20-30% humidity, 75° C.). Following 72 hours of exposure to environment, the animals were assessed for corneal staining upon exposure of the cornea to the dye methylene blue; less staining indicates less damage to the cornea. The rabbits were anesthetized by subcutaneous administration of ketamine hydrochloride (30 mg/kg) and xylazine (6 mg/kg). Sutures were placed in each upper and lower eyelid and lifted to form a corneal/conjunctival cup. Methylene blue dye (1 mL, 1% in distilled water) was added to the cup for five minutes and the excess removed by washing with 200 mL of BSS®. The contralateral eye was then stained using the same procedure. Rabbits were euthanized immediately following the staining procedure and the eyes were excised. The corneas were isolated and a 9.5 mm punch of the cornea was placed overnight in 2 mL of acetone/saturated sodium sulfate (7:3 v/v). The concentration of the extracted dye was determined spectrophotometrically by measuring its absorbance at $\lambda$=660 nanometers (A660). Percent inhibition was calculated as $\{1-[(A660_{test\ item}-A660_{Normal})/(A660_{BSS}-A660_{Normal})]\} \times 100$, where $A660_{test\ item}$ is the absorbance of dye from ConA-injected eyes dosed with compound 1, $A660_{Normal}$ is the absorbance of dye from saline-injected eyes, and $A660_{BSS}$ is the absorbance of dye in ConA-injected eyes dosed with 0.064% ethanol/BSS® solution vehicle. A higher percent inhibition of staining indicates more protection of the cornea from damage.

A second group of animals was evaluated for tear film quality by measuring each animal's tear breakup time (TBUT). Using the same experimental protocol as above for inducing rabbit ocular damage, TBUT was determined daily by instilling 5 µL of sodium fluorescein into the cul de sac and manually blinking the lids to distribute the fluroescein within the tear film. Under slit lamp observation, the eye was held open and the time whereby one or more black spots or streaks appeared in the precorneal tear film was recorded. The rabbits were euthanized 3 days following ConA injection. Larger TBUT values indicate better tear film quality and more protection from ocular damage. TBUT data is expressed as % of baseline, with baseline TBUT being that observed for saline-injected, vehicle-treated eyes.

The % inhibition of corneal staining and TBUT data are presented below in table 1, with 15S-HETE (Biomol Research Laboratories, Plymouth Meeting, Pa.) treatment of ConA-injected eyes used as a positive control.

TABLE 1

Effect of Compound 1 on Ocular Damage in Rabbits Induced by Lacrimal Gland ConA Injection Followed by Desiccation

| Compound | Concentration (µM) | % Inhibition of Corneal Staining, ±S.D.[a] | TBUT, % of Baseline, ±S.D. |
|---|---|---|---|
| 15S-HETE | 1 | 77 ± 18[b] | 54 ± 21[b] |
| 1 | 1 | 75 ± 12[b] | 67 ± 17[b] |
| 1 | 10 | 54 ± 9[b,c] | 45 ± 17[b] |
| 1 | 100 | 38 ± 34[b,c] | 51 ± 18[b] |

[a]S.D. = Standard Deviation.
[b]p < 0.01 (Dunnett's t-test) compared to vehicle.
[c]p < 0.01 (Dunnett's t-test) compared to 15S-HETE.

EXAMPLE 6

Protective Effect of Compound 1 in a Rat Model of Uveitis

Compound 1 was evaluated for its ability to suppress neutrophil influx into the rat eye in a model of endotoxin-induced uveitis. The compound was prepared at concentrations of 0.01%, 0.1%, 1.0% w/v in an ophthalmic suspension vehicle, and dexamethasone (Sigma-Aldrich Company, St. Louis, Mo.) formulated in the same vehicle served as reference compound. Uveitis was induced by subplantar injection of endotoxin (200 µg in 0.1 mL saline) in the right hind paw of female Lewis rats (5/group). Test compound of vehicle (5 µL) was administered topically to each eye of the experimental animals at the time of endoxtoxin injection and again 4 hours later. Twenty four hours post endotoxin injection, animals were sacrificed by $CO_2$ inhalation, and total ocular neutrophil (PMN) content was assessed indirectly by determination of myeloperoxidase activity. Ocular PMN content in each group was then compared with that observed in the vehicle-treated group using Dunnet's t-test. The results are shown below in table 2.

TABLE 2

Effect of Compound 1 on Endotoxin-Induced Uveitis in Rats Following Topical Ocular Administration

| Compound | Concentration (%, w/v) | Myeloperoxidase (µM/min/100 mg) (x ± standard deviation) | % inhibition |
|---|---|---|---|
| Carbopol Vehicle 1 | — | 164 ± 46 | — |
| | 0.01 | 143 ± 64 | 13 |
| | 0.1 | 161 ± 37 | 2 |
| | 1.0 | 97 ± 35 | 41* |
| Dexamethasone | 0.1 | 15 ± 7 | 91* |

*p < 0.01, Dunnett's t-test.

According to the methods of the present invention, a compound of formula I is administered in a pharmaceutically acceptable carrier for topical ophthalmic administration. The compositions are formulated in accordance with methods known in the art. The compositions may contain more than one compound of formula I. Additionally, the compositions may contain a second drug, other than a compound of formula I.

The compositions of the present invention contain a pharmaceutically effective amount of a compound of formula I. As used herein, "a pharmaceutically effective amount" means an amount sufficient to reduce or eliminate uveitis or dry eye symptoms. Generally, the compositions of the present invention will contain from 0.00001 to 0.01% of a compound of formula I for treating dry eye, and from 0.01% to 3% of a compound of formula 1 for treating uveitis. Preferably, the compositions of the present invention will contain from 0.00003 to 0.001% of a compound of formula I for treating dry eye, and from 0.1% to 1% of a compound of formula 1 for treating uveitis.

The compositions administered according to the present invention may also include various other ingredients, including but not limited to surfactants, tonicity agents, buffers, preservatives, co-solvents and viscosity building agents.

Various tonicity agents may be employed to adjust the tonicity of the composition, preferably to that of natural tears for ophthalmic compositions. For example, sodium chloride, potassium chloride, magnesium chloride, calcium chloride, dextrose and/or mannitol may be added to the composition to approximate physiological tonicity. Such an amount of tonicity agent will vary, depending on the particular agent to be added. In general, however, the compositions will have a tonicity agent in an amount sufficient to cause the final composition to have an ophthalmically acceptable osmolality (generally about 150-450 mOsm, preferably 250-350 mOsm).

An appropriate buffer system (e.g., sodium phosphate, sodium acetate, sodium citrate, sodium borate or boric acid) may be added to the compositions to prevent pH drift under storage conditions. The particular concentration will vary, depending on the agent employed. Preferably, however, the buffer will be chosen to maintain a target pH within the range of pH 5.5-8.

Other compounds designed to lubricate, "wet," approximate the consistency of endogenous tears, aid in natural tear build-up, or otherwise provide temporary relief of dry eye symptoms and conditions upon ocular administration to the eye are known in the art and may be included in the compositions of the present invention. Such compounds may enhance the viscosity of the composition, and include, but are not limited to: monomeric polyols, such as, glycerol, propylene glycol, ethylene glycol; polymeric polyols, such as, polyethylene glycol, hydroxypropylmethyl cellulose ("HPMC"), carboxy methylcellulose sodium, hydroxy propylcellulose ("HPC"), dextrans, such as, dextran 70; water soluble proteins, such as gelatin; and vinyl polymers, such as, polyvinyl alcohol, polyvinylpyrrolidone, povidone and carbomers, such as, carbomer 934P, carbomer 941, carbomer 940, carbomer 974P.

Topical ophthalmic products are typically packaged in multidose form. Preservatives are typically required to prevent microbial contamination during use. Suitable preservatives include: benzalkonium chloride, chlorobutanol, benzododecinium bromide, methyl paraben, propyl paraben, phenylethyl alcohol, edetate disodium, sorbic acid, polyquaternium-1, or other agents known to those skilled in the art. Such preservatives are typically employed at a level of from 0.001 to 1.0% w/v. Unit dose compositions of the present invention will be sterile, but typically will not contain a preservative and will be unpreserved.

Generally, 1-2 drops of such compositions will be administered from once to many times per day.

Representative eye drop formulations are provided below in Example 7 for treating dry eye and in Example 8 for treating uveitis.

EXAMPLE 7

| Ingredient | Concentration (% w/v) |
| --- | --- |
| Compound of formula I | 0.00003-0.001 |
| Ethanol | 0.03-0.2 |
| Boric Acid | 0.1-0.3 |
| Polyoxyl 40 Stearate | 0.1 |
| Edetate Disodium | 0.01 |
| Polyquaternium 1 | 0.001 |
| NaOH/HCl | q.s. to pH 6-8 |
| Purified Water | q.s. to 100% |

EXAMPLE 8

| Ingredient | Concentration (% w/v) |
| --- | --- |
| Compound of formula I | 0.1-1.0 |
| Hydroxypropyl methylcellulose | 0.1-0.5 |
| Dextran 70 | 0.1 |
| Sodium Chloride | 0.8 |
| Potassium Chloride | 0.12 |
| Dibasic Sodium Phosphate | 0.025 |
| Edetate Disodium | 0.01 |
| Polyquaternium-1 | 0.001-0.005 |
| NaOH/HCl | q.s. to pH 6-8 |
| Purified Water | q.s. to 100 |

This invention has been described by reference to certain preferred embodiments; however, it should be understood that it may be embodied in other specific forms or variations thereof without departing from its special or essential characteristics. The embodiments described above are therefore considered to be illustrative in all respects and not restrictive, the scope of the invention being indicated by the appended claims rather than by the foregoing description.

What is claimed is:

1. A method for the treatment of dry eye or uveitis in a mammal, which comprises topically administering to the eye of the mammal a composition comprising a pharmaceutically acceptable carrier and a pharmaceutically effective amount of a compound of formula I:

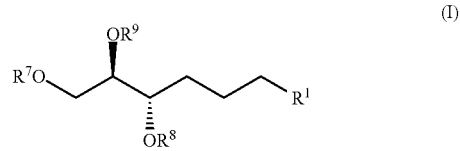

(I)

wherein
$R^1$ is $C_2H_5$, $CO_2R$, or a carboxylate salt of formula $CO_2^- R^+$;
$R^+$ is $Li^+$, $Na^+$, $K^+$, or $NH_4^+$;
R is H, $CH_3$, $C_2H_5$, n-$C_3H_7$, or i-$C_3H_7$; and
$R^7$, $R^8$, $R^9$ are H;
or $R^7$ and $R^8$ or $R^8$ and $R^9$ together constitute a carbonyl group (C=O), thus forming a cyclic carbonate;
or $OR^8R^1$ together form a lactone.

2. The method of claim 1, wherein a compound of formula I is used to treat uveitis.

3. The method of claim 1, wherein a compound of formula I is used to treat dry eye.

4. The method of claim 2, wherein the compound is selected from the group consisting of:

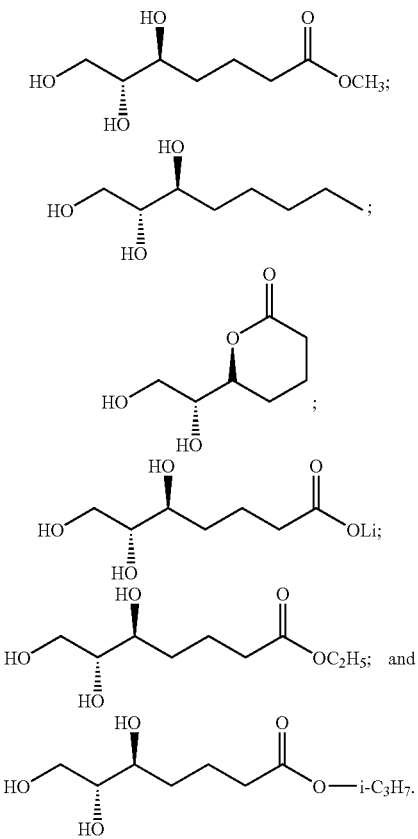

5. The method of claim 3, wherein the compound is selected from the group consisting of:

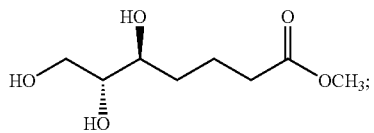

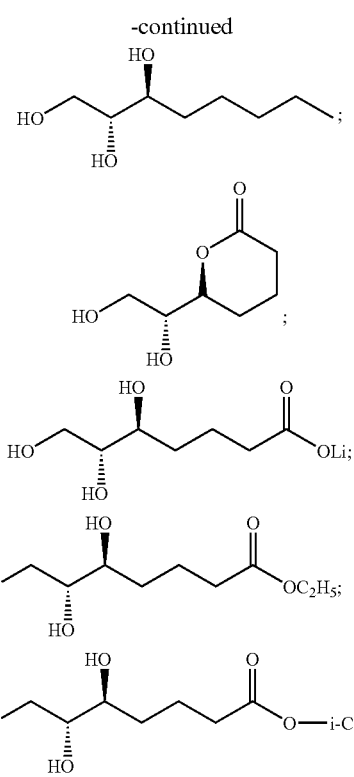

6. The method of claim 2, wherein the pharmaceutically acceptable amount is from 0.1 to 1% (w/v).

7. The method of claim 3 wherein the pharmaceutically acceptable amount is from 0.00003 to 0.001% (w/v).

8. The method of claim 6, wherein the pharmaceutically acceptable carrier comprises one or more ingredients selected from the group consisting of surfactants; tonicity agents; buffers; preservatives; co-solvents; and viscosity building agents.

9. The method of claim 7, wherein the pharmaceutically acceptable carrier comprises one or more ingredients selected from the group consisting of surfactants; tonicity agents; buffers; preservatives; co-solvents; and viscosity building agents.

* * * * *